United States Patent
Williams (10) Patent No.: US 6,818,895 B2
(45) Date of Patent: Nov. 16, 2004

(54) RESPIRATORY GAS ANALYZER

(75) Inventor: Kevin G. Williams, Pinole, CA (US)

(73) Assignee: Andros Incorporated, Berkeley, CA (US)

( * ) Notice: Subject to any disclaimer, the term of this patent is extended or adjusted under 35 U.S.C. 154(b) by 0 days.

(21) Appl. No.: 10/407,787

(22) Filed: Apr. 4, 2003

(65) Prior Publication Data

US 2003/0205673 A1 Nov. 6, 2003

Related U.S. Application Data

(63) Continuation of application No. 09/687,927, filed on Oct. 13, 2000, now abandoned.

(51) Int. Cl.⁷ .............................................. G01N 21/35
(52) U.S. Cl. ................... 250/343; 250/339.07; 250/345
(58) Field of Search .......................... 250/343, 339.07, 250/345; 6/345

(56) References Cited

U.S. PATENT DOCUMENTS

| | | | |
|---|---|---|---|
| 4,346,296 A | 8/1982 | Passaro et al. | |
| 4,423,739 A | 1/1984 | Passaro et al. | |
| 5,081,998 A | 1/1992 | Yelderman et al. | |
| 5,095,913 A | 3/1992 | Yelderman et al. | |
| 5,281,817 A | 1/1994 | Yelderman et al. | |
| 5,282,473 A | 2/1994 | Braig et al. | |
| 5,296,706 A | 3/1994 | Braig et al. | |
| 5,811,812 A * | 9/1998 | Williams et al. | 250/343 |
| 6,043,493 A * | 3/2000 | Kim et al. | 250/349 |
| 6,277,081 B1 * | 8/2001 | Susi et al. | 600/532 |

* cited by examiner

Primary Examiner—Constantine Hannaher
Assistant Examiner—Shun Lee
(74) Attorney, Agent, or Firm—Coudert Brothers LLP (57) ABSTRACT

An infrared gas analyzer includes an infrared source for emitting infrared energy, a sample cell for gases to be analyzed in the path of infrared energy emitted by the source and an assembly having first and second detectors also in the path of infrared energy and a third detector out of the path of infrared energy, mounted within the assembly and in close thermal proximity to each other and being responsive to impinging infrared energy to produce an electrical response. All detectors are sandwiched between a base and a single window that overlies them. The analyzer further includes a narrow band filter corresponding to an absorption wavelength band for a gas of interest and a narrow band reference filter corresponding to a reference wavelength band. Each of the narrow band filters are positioned outside the assembly and between the assembly and the source in the path of infrared energy.

5 Claims, 6 Drawing Sheets

RESPIRATORY GAS ANALYZER

This application is a continuation of application Ser. No. 09/687,927, filed Oct. 13, 2000, now abandoned.

FIELD OF THE INVENTION

This invention relates generally to non-dispersive infrared spectrophotometers. More particularly, this invention relates to an improved gas analyzer which measures the concentration of one or more gases in a gas mixture present in a sample cell.

BACKGROUND OF THE INVENTION

Gas analyzers of the non-dispersive type typically operate on the premise that the concentration of a designated gas can be measured: (1) by passing a beam of infrared radiation through the gas, and (2) ascertaining the attenuation of the energy in a narrow wavelength band absorbable by the designated gas with a detector capable of generating an electrical output signal proportioned to the energy in the band passing through the gas. Examples of such analyzers are disclosed in U.S. Pat. Nos. 4,346,296, 4,423,739, and 5,811,812.

NDIR gas analyzers utilize an IR source, typically an electric heater, to provide IR radiation through a gas sample contained in a sample cell for detection by a detector. The amplitude of the signal detected by the detector at a wavelength, which corresponds to the absorption wavelength of a gas of interest, provides an indication of the concentration of that gas in the sample. Concentration of gases, such as CO, $CO_2$, hydrocarbons (HCs), anesthetic agent gases, exhaust gases, Freon, or other gases can be determined by IR radiation spectroscopes. Each species of gas typically has one or more distinct IR absorption characteristics and better absorbs IR radiation at or near a particular wavelength. The absorption of IR radiation at a frequency corresponding to a characteristic absorption wavelength of a particular gas species decreases, as the concentration of that species in the gas sample. In other words, the amplitude of the signal detected by the IR detector at a wavelength corresponding to a characteristic absorption wavelength of a particular gas species is inversely proportional to the concentration of that species in the gas sample.

Medical applications of these gas analyzers include the monitoring of end-tidal carbon dioxide, i.e., the concentration of carbon dioxide in a patient's exhalations. This expired carbon dioxide level can be employed by medical personnel to monitor the operation of a ventilator to assist a patient's breathing. A sample cell is designed to be inserted into the airway of a patient on a ventilator and includes a pair of opposed windows having a line of sight positioned so as to allow a beam of infrared radiation to pass therethrough. The sample cell confines the expired gases to a flow path with a precise, transverse dimension, and it furnishes an optical path between an infrared radiation emitter or source, and an infrared radiation detector assembly having a plurality of detectors electrically responsive to impinging radiation.

The infrared radiation traverses the gases in the sample cell where it is attenuated because part of the radiation is absorbed by the designated gas or gases being analyzed. The attenuated beam of infrared radiation is then filtered to eliminate energy at wavelengths lying outside the narrow band absorbed by a particular gas being measured. The infrared radiation in that band impinges upon a detector which consequently generates an electrical signal proportional in magnitude to the intensity of the infrared radiation impinging upon it.

Typically, a narrow band optical filter is positioned in front of the detector to pass a narrow band of only those wavelengths of infrared radiation absorbed by the gas or gases of interest. For example, a narrow band filter with a center wavelength of approximately 4.3 microns is conventionally selected for $CO_2$ absorption. The remaining infrared radiation in the band impinges upon the detector. The detector then generates an electrical response proportional in magnitude to the intensity of the infrared radiation impinging upon it which can be related to the concentration of $CO_2$.

The reading at the detector is subject to system sensitivities which are independent of gases within the gas sample. Such system sensitivities include absorption by contaminants on the gas sample cell windows, IR dissipation due to obstructions in the radiation path, effectiveness of the manner by which the radiation is collected after passing through the sample cell, the sensitivity of the detector, and the gain of the signal processing electronics. In order to account for system sensitivities in the concentration readings, a reference detector is used. The reference detector is intended to provide a measure of the intensity of the infrared radiation in the optical path at a wavelength which is unaffected by the presence of gases likely to be in the sample cell. Therefore, the detector signal measured by the reference detector provides a measure of the basic sensitivity of the system to infrared radiation in general. That is, it provides a measure of the strength of the radiation of the IR source, the attenuation of the radiation by (non-spectral) contamination and the like on the infrared transparent windows in the sample cell, and further provides a measure of the sensitivity of the detectors as well as the gain of the processing electronics.

The band width and the center of the band for the reference detector are selected to be in an inifrared non-absorptive region for typical gas samples to be tested. Otherwise, the reading by the reference detector would be influenced by the concentration of any gases in the gas sample which absorb IR radiation before it reaches the reference detector. Therefore, it is important that the reference detector detect IR radiation at a wavelength which is displaced from the absorption wavelengths of the gases likely to be present in the gas sample.

However, it is also important that the characteristic absorption wavelength at which the reference detector detects IR radiation not be widely spaced from the characteristic absorption wavelengths of the gases of interest. This is because some system sensitivities are highly dependent on the wavelength of IR radiation used. Therefore, it is preferable to use a reference wavelength that is close to, but does not overlap, the characteristic absorption wavelength of any of the gases of interest, to increase the likelihood that the reference is a true reference which is unaffected by the concentration of the gases in the gas sample.

The output signals generated by the detectors are sent to a signal processor. The signals are ratioed to eliminate errors in the measured concentration of the gas of interest. These errors are attributable to such factors as foreign substances (e.g., condensation on the sample cell windows) and other instabilities in the infrared source and/or the detectors. A gas analyzer may also employ additional optical components, such as beam splitters, lens configurations, and the like, to increase the sensitivity and accuracy of the detectors. For example, a dichroic beam splitter may be incorporated in the beam path ahead of the detectors.

Thermopile detectors, i.e., a detector comprised of a plurality of interconnected thermocouples, are commonly used for detecting infrared radiation. The plurality of thermocouples develop a voltage output in response to impinging infrared radiation. Thermopile detectors, however, suffer from so called "drift" which results in a slow variation in the voltage output of the detectors as a consequence of variations in ambient temperature and stray radiation. Thus, the measurement of gas concentrations as an absolute or steady state DC output may be difficult because of the thermal drift issue.

Means of addressing thermal drift in thermopile detectors include modulating or chopping the incident infrared beam, either by shutter type devices or by modulating the output of the infrared source of energy. Simpler systems have been designed which involve totally blocking one of the thermopile detectors and using the output thereof as a zeroing signal for comparison with the output of the other detector or detectors. Heretofore, such attempts have produced error signals due to uneven heating of the substrate. Partially attenuating the signal falling upon the zeroing detector has been suggested, but configurations taught by the prior art in which such an expedient is employed have demonstrable drawbacks.

Accordingly, it is an object of the present invention to provide an improved infrared spectrophotometer.

Another object of the invention is to provide an improved infrared spectrophotometer providing a steady state DC signal representative of gas concentration from detectors corresponding to gases of interest.

Another object of the invention is to provide an improved infrared spectrophotometer and a detector assembly therefore which effect substantial cost saving over that provided by prior art configurations.

DESCRIPTION OF THE DRAWINGS

Other objects of the invention will become apparent to those skilled in the art from the following description, taken in connection with the accompanying drawings wherein.

SUMMARY OF THE INVENTION

Very generally, the infrared spectrophotometer of the invention comprises an infrared source for emitting infrared energy. A sample cell is provided for containing gases to be analyzed and is positioned in the path of infrared energy emitted by the source. A detector assembly includes first, second and third thermopile detectors mounted in thermal proximity to each other and being responsive to impinging infrared energy to produce an electrical response. The first and second detectors are positioned in the path of infrared energy emitted by the source and the third detector is positioned out of the path of infrared energy emitted by the source. The spectrophotometer further comprises a narrow band filter corresponding to an absorption wavelength band for a gas of interest and a narrow band reference filter corresponding to a reference wavelength band. Each of the narrow band filters are positioned between the detector assembly and the source in the path of infrared energy emitted by the source on to a respective one of the first and second detectors.

DETAILED DESCRIPTION OF THE INVENTION

Figure 1:
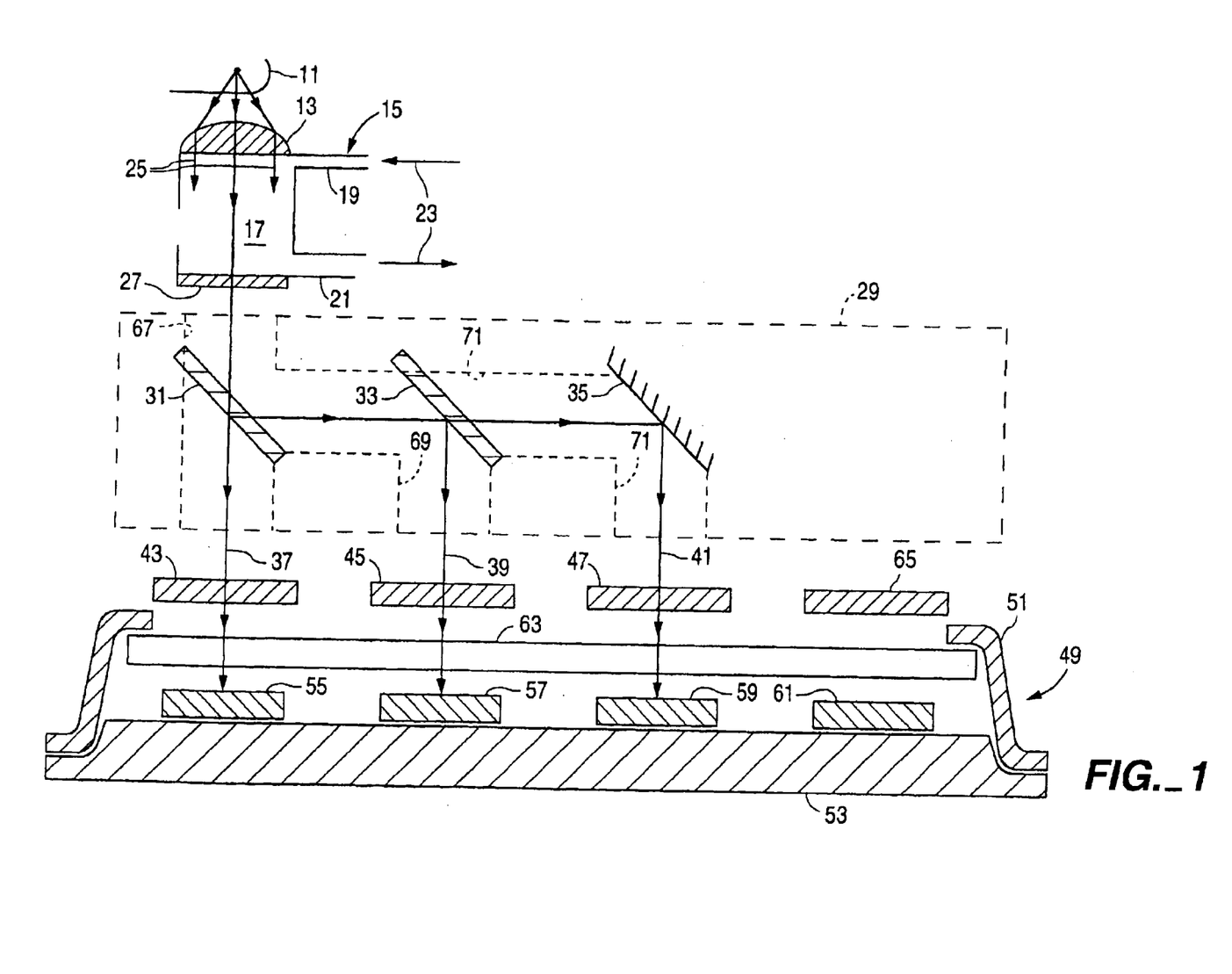
FIG. 1 is a schematic diagram of an improved spectrophotometer constructed in accordance with the invention.

FIG. 1 is a schematic diagram of an apparatus constructed in accordance with the invention. Infrared energy from a source 11 is collimated by a collimating lens 13 and directed through a sample cell 15. The sample cell defines a chamber 17 for containing a volume of gas to be analyzed. Gas enters the chamber 17 through an inlet passage 19 and exits the chamber through an outlet passage 21 as shown by the arrows 23. Infrared energy shown by the arrows 25 passes through the gas in the chamber 17 and exits through an exit window 27.

Sample cells such as that depicted schematically at 15, and infrared energy sources such that depicted schematically at 11, are well known to those skilled in the art. The structure and configuration of these elements may be selected, as is well known to those skilled in the art, in accordance with the needs of the particular system, such as the type of gases to be analyzed, the flow rate of the gas to be analyzed, and so forth.

In a preferred form of the invention, a major portion of the optics of the spectrophotometer is contained and supported in an optical block, namely, a multi-part metal or plastic block having passages machined therein and supporting various optical elements. In the illustrated embodiment, this block is indicated schematically by the dotted rectangle 29 and contains and supports two dichroic mirrors 31 and 33 and a reflecting mirror 35. The various optical axes showing the paths of infrared radiation are designated by the dark lines having the spaced arrowheads. It should be understood, however, that in the preferred embodiment of the invention, the optical axes may differ from what is shown schematically, and also may contain multiple reflections to an array of detectors which is not linear, rather than reflections to a linear array as shown.

Preferably, the optical paths of the infrared radiation are confined by a series of highly reflecting cylindrical surfaces, (commonly referred to as light pipe optics). In the case of the sample cell 15, a stainless steel tube may be used that is of the order of 1 cm in length and which is provided with a highly polished interior surface. The remaining light pipes forming the optical paths are preferably formed within the optical block 29, as described more particularly below.

The dichroic mirror 31 is positioned to receive the infrared energy passing through the exit window 27 of the sample cell 15. A portion of this energy at a first preselected wavelength passes through the mirror 31 and vertically downward as shown in FIG. 1. A portion of the energy is reflected at roughly 90° to the second dichroic mirror 33. The energy impinging upon the second dichroic mirror is split so that a portion is reflected vertically downward and so that a portion passes through the mirror to the mirror 35. The mirror 35 reflects the energy impinging upon it vertically downward. In a preferred form of the invention, two reflecting mirrors are utilized in this particular path of energy such that the optical axis is turned through 90° twice between the dichroic mirror 33 and the reflecting mirror 35.

The net result of the above described optical arrangement is that there are three optical paths 37, 39 and 41 which emerge from the optical block 29. Each of these energy paths then passes through a respective one of three narrow band filters 43, 45 and 47. As will be explained, each of these filters is selected to pass a narrow wavelength band of infrared energy corresponding either to the characteristic absorption wavelength band of a gas of interest or to a reference wavelength band.

A detector assembly 49 is positioned in order to provide an electrical response to the energy emerging from the narrow band filters 43, 45 and 47. The detector assembly includes a housing 51 which is generally annular and which is mounted on a base plate 53. The base plate 53, in the preferred form of the invention, is circular and has mounted to its upper surface four detectors 55, 57, 59 and 61. In the preferred embodiment, the detectors are arranged quadrilaterally as may be seen in FIGS. 2 and 5. An infrared transparent window 63 of a material which is preferably antireflection coated silicon is supported by the housing 51 and overlies the detectors 55, 57, 59, and 61 positioned between the detectors and the narrow band filters 43, 45, 47. A reflective mirror 65 is mounted just outside the detector assembly in the same plane as the narrow band filters and directly above the detector 61. As may be seen, the detector 61 and mirror 65, the underside of which is reflective, are positioned to be out of the path of infrared energy emitted by the source 11. On the other hand, the detectors 55, 57 and 59 are positioned in alignment with the respective narrow band filters 43, 45 and 47 to receive infrared energy in the energy paths 37, 39 and 41, respectively.

In the preferred form of the invention, the dichroic mirrors 31 and 33 are selected so as to provide close to 100% transmission efficiency within the spectral pass band of the corresponding narrow band filters 43 and 45. In the preferred form of the invention, the dichroic mirror 31 transmits 90% of the light within the pass band of the narrow band filter 43 to the detector 55. This same dichroic mirror 31 reflects 100% of the light within the pass band of the narrow band filter 45 and within the pass band of the narrow band filter 47. The dichroic mirror 33 reflects 100% of the light within the pass band of the filter 45 onto the detector 57. The dichroic mirror 33 further transmits 90% of the light within the pass band of the narrow band filter 47 onto the detector 59.

Each of the detectors 55, 57, 59, and 61, are preferably thermopile detectors. A thermopile detector typically is comprised of a plurality of thin film layers of dissimilar materials arranged so that all odd numbered junctions are heated substantially differently by incident radiation than the even numbered junctions. Typically this is accomplished by blocking incoming radiation on the even numbered junctions while exposing the odd numbered junctions, or vice versa. Thus, a net voltage difference is created as a result of the temperature difference between the so-called hot and cold junctions. This electrical response is used as a measure of the amount of radiation reaching a hot junction.

Because other sources of heat besides radiation can be thermally conducted into the detectors, the arrangement may be subject to so-called thermal "drift" which makes it difficult to relate the direct current output of a detector to an absolute measurement of gas concentration. The effect of thermal drift can be offset in a number of ways. For example, the detector elements can be connected electrically in a so-called back-to-back configuration, thus resulting in an output signal representing the difference in signal produced by the detector elements. By fully blocking the radiation incident on one of the detector elements, such a device can be used as a radiometer. Other ways of improving DC stability can include connecting multiple pairs of back-to-back connected detectors, utilizing narrow band filters which are placed in close proximity to each pair of detectors, and by controlling and attenuating substantially the intensity of radiation impinging on one of the detectors to use such a detector as a reference or zeroing element. All of these approaches have particular drawbacks.

In accordance with the present invention, thermal stability is achieved by mounting the detectors in close proximity to the window 63 and by locating the narrow band filters outside of the detector assembly. Additionally, the detector 61 is positioned to be totally out of the path of incident infrared radiation emanating from the source 11. Moreover, the mirror 65 reflects back upon the detector 61 so that the detector 61 sees an image of itself only, but is still in thermal proximity to the other detectors. By thermal proximity it is meant that the temperature of those elements in thermal proximity remains substantially the same under all operating conditions, except for radiation emanating from the source 11. The detectors are all mounted in the same plane and are secured to a single header. The infrared window is mounted in thermal proximity to the detectors. Thus, all detectors have essentially the same amount of heat conducted, convected and radiated to them from the header and the window. Only those detectors which are in the path infrared energy receive additional radiated heat and that energy is only at the transmitted wavelength band of the corresponding narrow band detector. In processing the electrical signals, either electronically or in software, the voltage generated by the detector 61 is subtracted from the voltages generated by the other detectors, thus achieving thermal stabilization.

Figure 2:
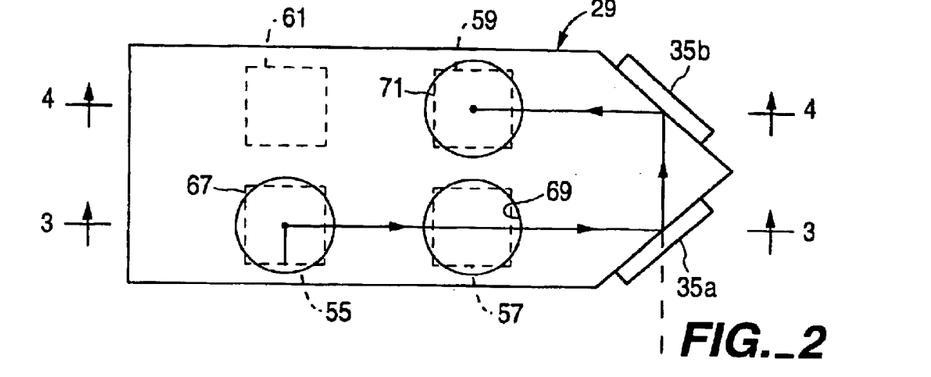
FIG. 2 is a plan view of the lower portion of the spectrophotometer of FIG. 1.
Figure 3:
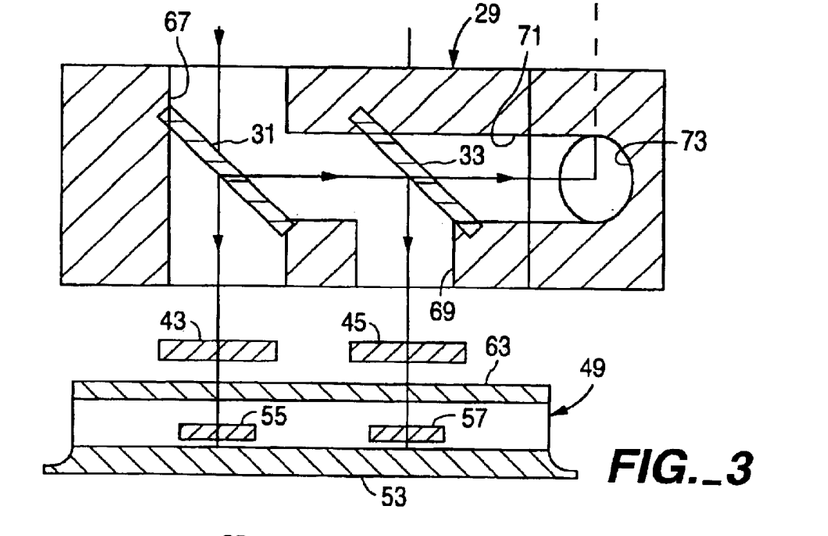
FIG. 3 is a sectional view taken along the line 3—3 of FIG. 2.

Referring now to FIG. 2, a plan view of the optical block 29 is shown. The optical block is comprised of plastic of a suitable type, such as ABS. The openings or light pipes 67, 69 and 71 are formed in the block 29 and are preferably provided with a gold film plated thereon in accordance with known techniques to achieve high reflectivity. The view in FIG. 2 is somewhat simplified but shows the location of the respective detectors in phantom. Also, dual reflective mirrors are shown in FIG. 2 as 35a and 35b to reflect the light through two 90° turns. The block 29 is manufactured in three separate pieces, separable along the section lines 3—3 and 4—4. In FIG. 3, it may be seen that the dichroic mirrors 31 and 33 are supported in the light pipes 67 and 69, respectively. A horizontal light pipe formed internally within the block connects the two light pipes 67 and 69. The light pipe 71 extends horizontally within the block to a transverse light pipe 73 which turns the beam 90° as a result of the reflection provided by the mirror 35a and again through 90° resulting from the reflection provided by the mirror 35b. Radiation emerges from the optical block 29 downwardly through the narrow band filters 43 and 45 to the detector assembly 49, passing through the window 63 thereof onto the detectors 55 and 57.

Figure 4:
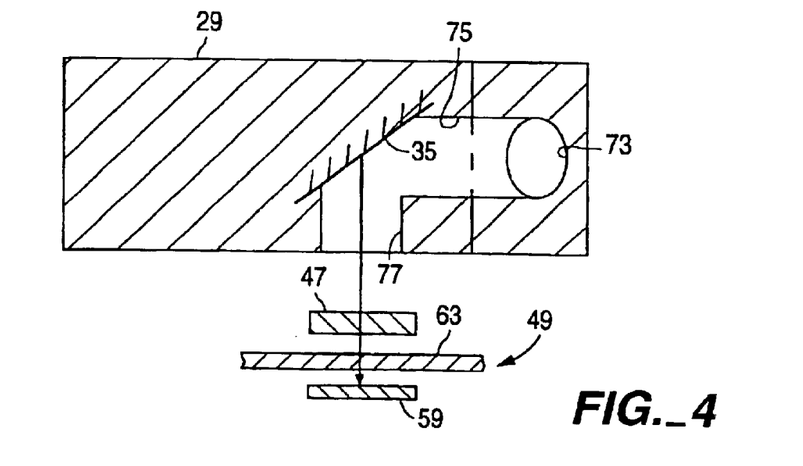
FIG. 4 is a sectional view taken along the line 4—4 of FIG. 2.

As may be seen in FIG. 4, radiation reflected by the mirror 35b passes through a further horizontal light pipe 75 to the mirror 35 from whence it is deflected downwardly through a further light pipe 77 to the narrow band filter 47 and thence to the detector assembly 49.

Figure 5:
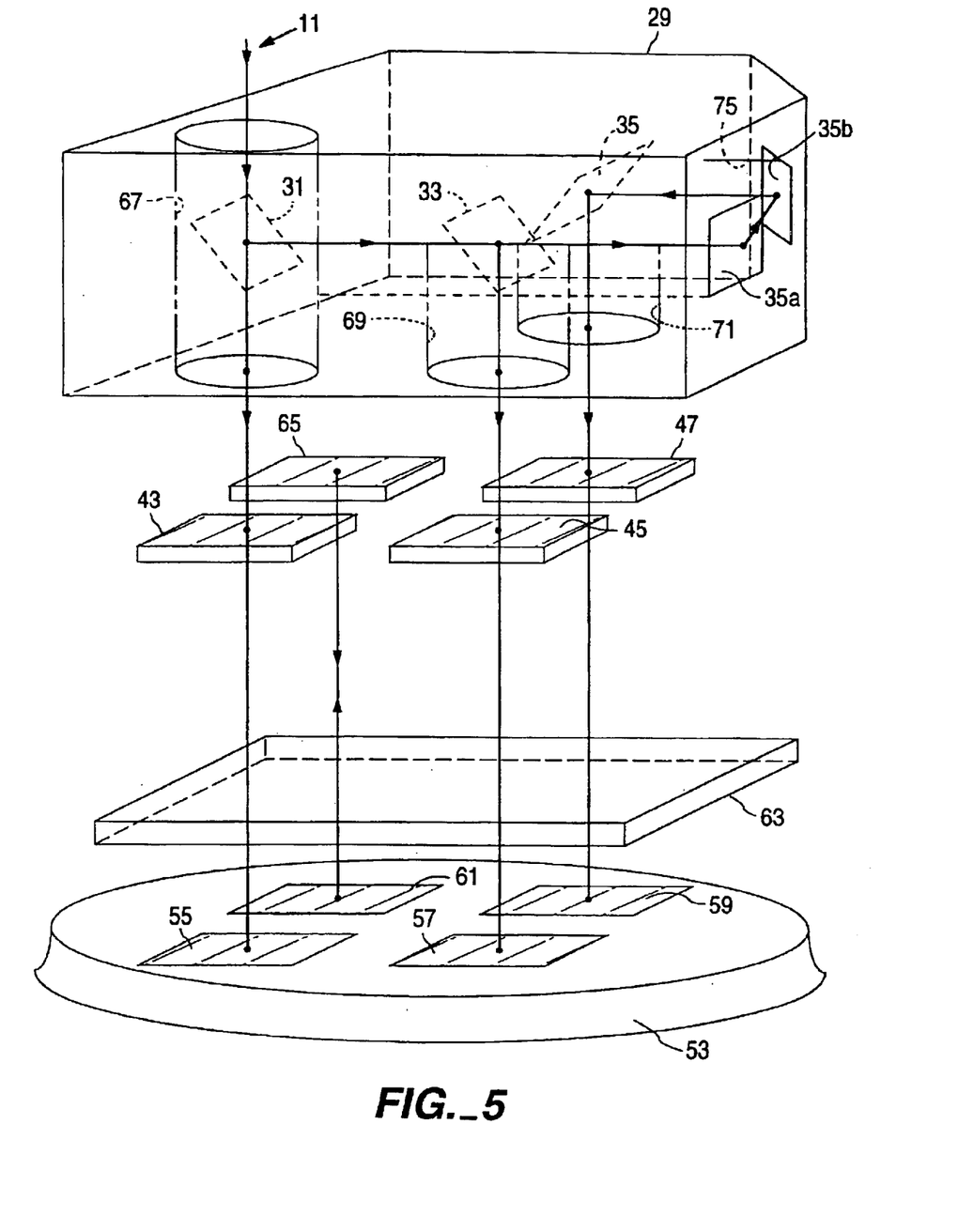
FIG. 5 is an isometric diagrammatical view of a preferred embodiment of the gas analyzer of the invention.

In FIG. 5, the arrangement of components is illustrated isometrically to provide a general idea of the relative positions thereof as previously described. Once more, it may be seen that the detectors are supported on a base plate thermally juxtaposed to a transparent window. By placing the narrow band filters outside of the detector assembly, the cost of the detector assembly itself is relatively low. Thus, failure of any of the elements in the detector assembly results in a relatively low cost repair and does not require replacement of high cost narrow band filters as is the case with some prior art designs.

Figure 6:
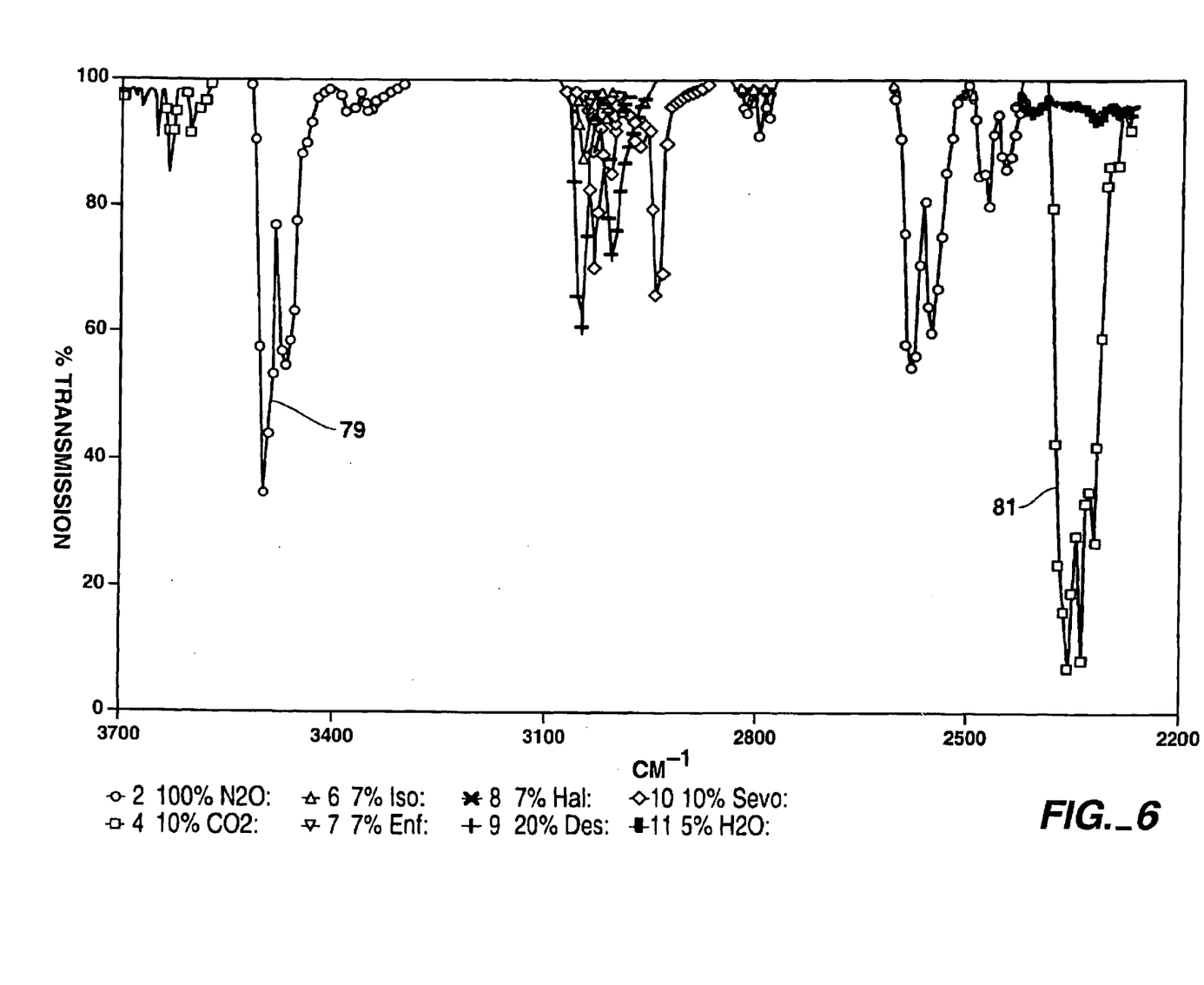
FIGS. 6–8 are graphs illustrating spectral transmission properties of gases, and of the mirrors and filters in a preferred form of the gas analyzer of the invention.

For purposes of illustration, there will now be described a specific method and apparatus for monitoring the concentration of nitrous oxide and carbon dioxide in a sample cell. In FIG. 6, the transmission spectra of gases typically present in the expired breath of a patient under anesthesia are illustrated. Listed below are the constituent gases for which the absorption is plotted and the percentage concentration of the gas used in obtaining the plotted relevant spectrum. As may be seen from the plot, the major peaks of gas absorption are for the nitrous oxide and carbon dioxide. These are illustrated at 79 and 81 respectively. The other gases present in typical expired breath of a patient under anesthesia are also illustrated as coded by the symbols in the list appearing below the graph.

Figure 7:
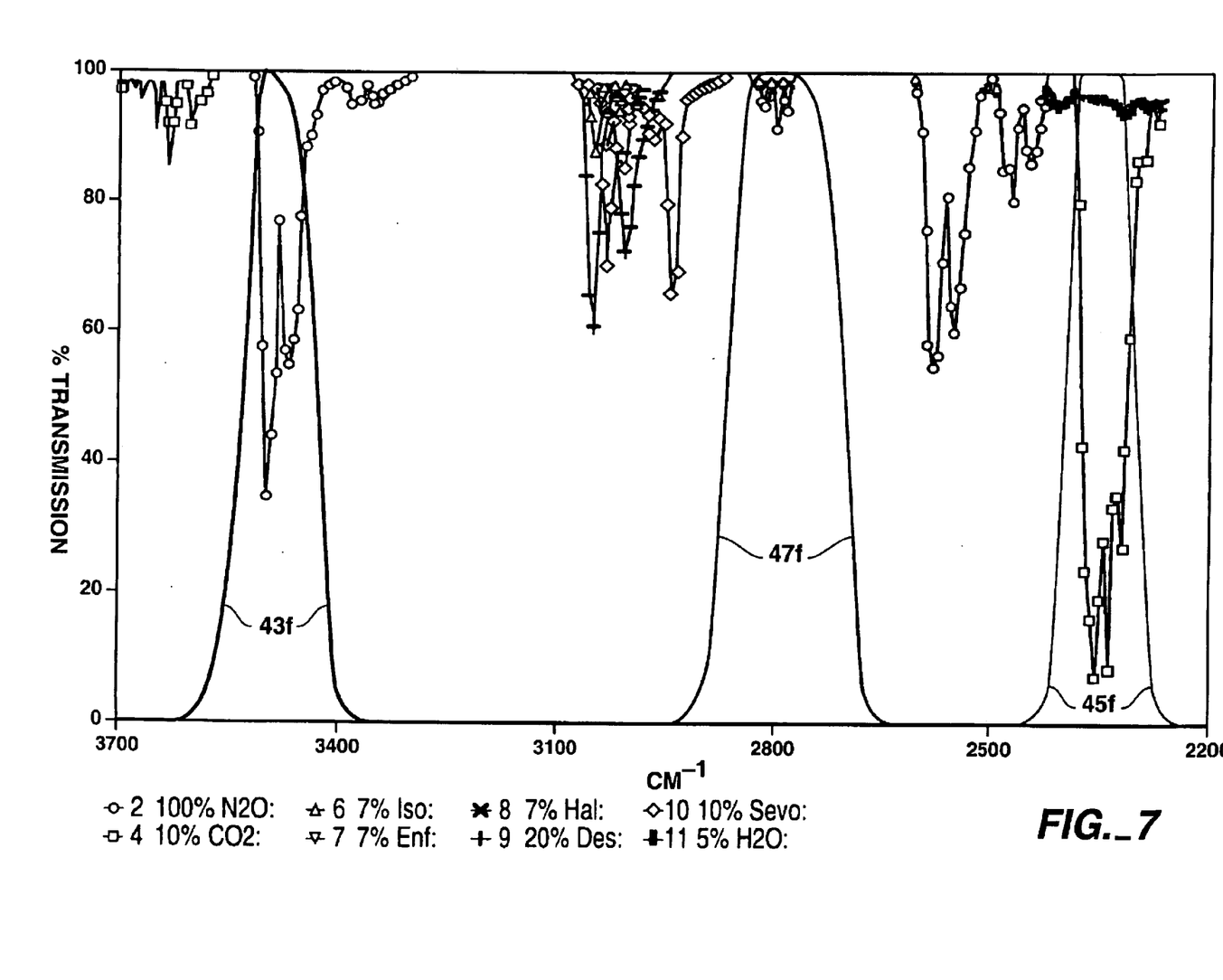

In the FIG. 7, the absorption spectra of FIG. 6 are illustrated superimposed upon the bandpass curves of the narrow band filters 43, 45, and 47. These curves are illustrated respectively at 43f, 45f, and 47f. It will be seen that the reference pass band 47f is positioned between the nitrous oxide pass band 45f and the carbon dioxide pass band 43f. Nevertheless, there is some interference in the pass band 47f as a consequence of absorption spectra produced by the presence of nitrous oxide and certain anesthetic agents. Since anesthetic agents are not measured in the gas analyzer described, correction of such interference may be accomplished by supplying concentration information on anesthetic agents derived by other suitable means. Such means are well known to those skilled in the art, and include data derived from the concentration of anesthetic agents being supplied to the patient, or a separate anesthetic agent analyzer measuring the concentration of such agents in the same gas stream.

With respect to the absorption of nitrous oxide in the reference pass band 47f, the absorption in this band is only a few percent of the radiation being absorbed in the pass, band 45f and may be readily be corrected for, either by a suitable constant or by relating the measurement of nitrous oxide being performed simultaneously as a consequence of the nitrous oxide detector output.

Figure 8:
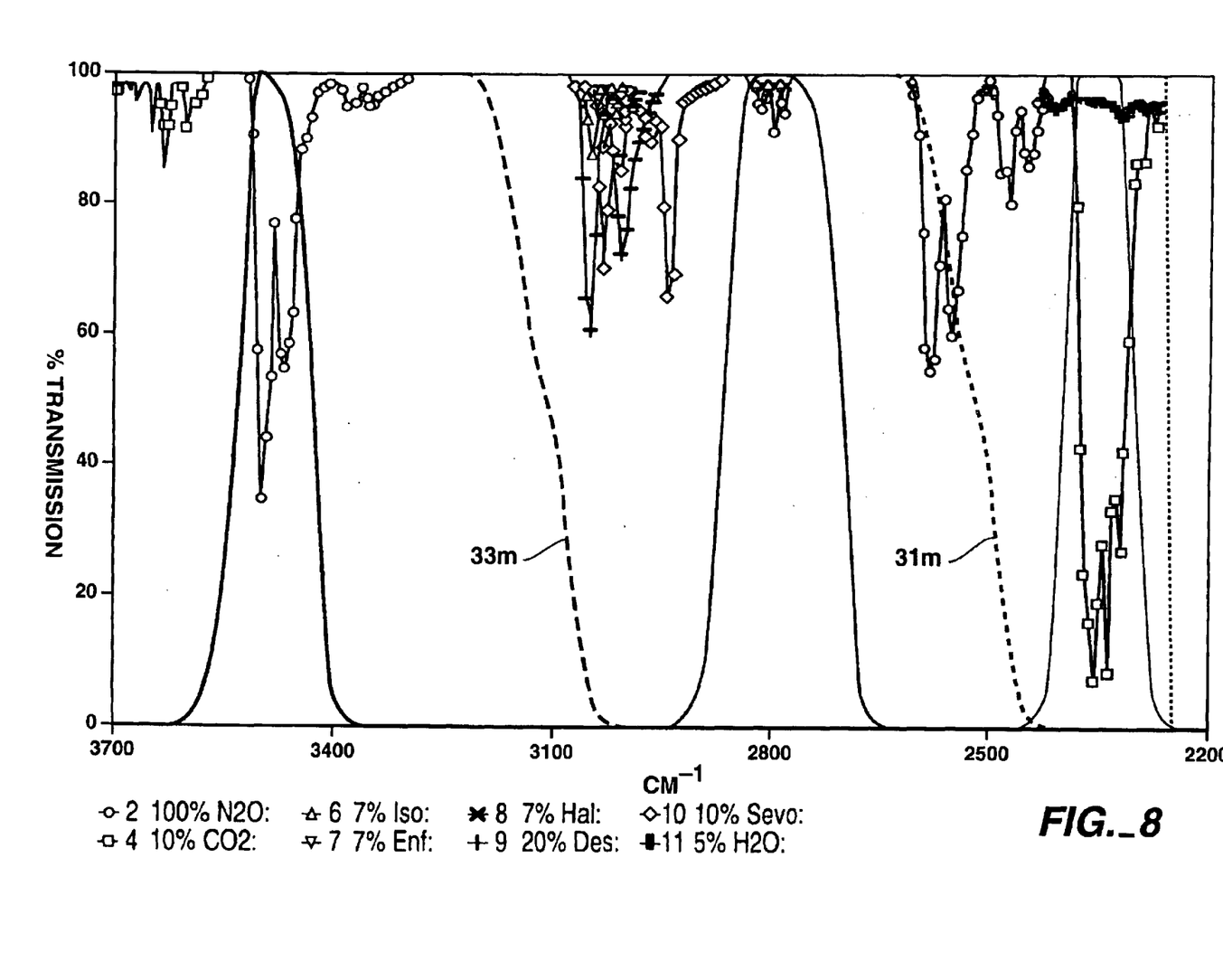

In FIG. 8, the transmission spectra of the gases of FIG. 6, the pass band curves of the narrow band filters 43, 45 and 47, and the transmission of the dichroic mirrors 31 and 33 are all superimposed. The pass, non-pass transition for the dichroic mirror 31 occurs between about 2,400 and 2,650 cm$^{-1}$ and is shown by the curve or line 31m. Similarly, the transition slope for the dichiroic mirror 33 for nitrous oxide is shown at 33m. Thus, the mirror 33 functions to pass substantially 100% of infrared energy below about 3,200 cm$^{-1}$ and reflect substantially 100% of the energy above the wavelength of about 3,200 cm$^{-1}$. Similarly, the mirror 31 functions to pass substantially all of the energy above 2,650 cm$^{-1}$ and to reflect substantially all of the energy below about 2,400 cm$^{-1}$.

Although the foregoing preferred embodiment of the invention is designed for measuring the concentration of carbon dioxide and nitrous oxide, it will be apparent to those skilled in the art that the infrared spectrophotometer of the invention may be readily adapted for the measurement of other gases by appropriate selection of the narrow band filters and dichroic mirrors, dependent upon the transmission spectra of the gases present in the sample to be analyzed. By constructing the infrared spectrophotometer in accordance with the invention, all sources of thermal and optical energy reaching the detectors producing the gas concentration output and reaching the reference detector are essentially the same, except that the energy transmitted by the narrow band filters in the optical path of the gas concentration detectors will be different. By using a single or background detector that is outside the field of view of the infrared source, compensation for all background optical radiation and thermal effects on the detectors may be effected. This makes possible DC measurements at two or more wavelengths within a single package. The cost of the detector assembly is substantially reduced by making it possible to locate the relatively expensive narrow band interference filters outside of the detector assembly itself. Thus, the cost impact of a failure of any of the detector elements is substantially reduced. By mounting all of the thermopile detectors to the same single header or support element, and by mounting a single infrared transmitting window in close proximity to the thermopiles, all detectors have essentially the same amount of heat conducted, convected, and radiated to them from the header and the window. Thus, variations are confined to the incident radiation. For the background detector which is located outside the field of view of the infrared source, the mirror stabilizes the incident radiation by reflecting back to that detector substantially 100% of the radiation incident on the detector side. Thus, the only difference in energy reaching the various detectors is energy that is transmitted to the relevant detectors through their corresponding narrow band filters.

The resulting infrared spectrophotometer produces a DC direct indication of gas concentration in a very stable thermal environment free from thermal drift. Various modifications of the invention will become apparent to those skilled in the art from the foregoing description and accompanying drawings. Such modifications are intended to fall within the scope of the appended claims.

What is claimed is:

1. An infrared gas analyzer comprising:
   (a) an infrared source for emitting infrared energy;
   (b) a sample cell for containing gases to be analyzed positioned to be in the path of infrared energy emitted by said source;
   (c) a detector assembly comprised of a housing, a base, at least first, second and third thermopile detectors supported on said base, and an infrared transparent window on the opposite side of said detectors from said base, said base, detectors and window being in close thermal proximity to each other and being responsive to impinging infrared energy to produce an electrical response, said detector assembly being unitary and detachably mounted in said infrared gas analyzer, said first and second detectors being positioned in the path of infrared energy emitted by said source, and
   (d) a wavelength narrow band filter corresponding to an absorption band for each of the gases of interest and a narrow band reference filter corresponding to a reference band, each of said narrow band filters being positioned outside of said detector assembly and between said detector assembly and said infrared source in the path of infrared energy emitted by said source on a respective one of said first and second detectors, said third detector being positioned outside of the path of infrared energy emitted by the source and out of alignment with any of laid narrow band filters, whereby the electrical response generated by said third detector may be subtracted from the electrical responses generated by said first and second detectors to achieve thermal stablization.

2. A gas analyzer according to claim 1 including a plurality of dichroic mirrors for parsing the infrared energy between said first and second detectors.

3. A gas analyzer according to claim 2 wherein said dichroic mirrors are supported in an optical block.

4. A gas analyzer according to claim 1 including a fourth detector positioned in the infrared path, said fourth detector being adapted for detecting carbon dioxide, said first detector being adapted for detecting nitrous oxide, and said second detector being adapted for detecting a reference wavelength bandwidth.

5. A gas analyzer according to claim 1 including a mirror positioned adjacent said detector assembly for reflecting substantially all infrared radiation emanating from the region of said third detector back onto said third detector.

* * * * *